United States Patent [19]

Foster et al.

[11] Patent Number: 4,968,626
[45] Date of Patent: Nov. 6, 1990

[54] DNA SEQUENCE CODING FOR PROTEIN C

[75] Inventors: Donald C. Foster, Seattle; Earl W. Davie, Bellevue, both of Wash.

[73] Assignee: Board of Reagents of the University of Washington, Seattle, Wash.

[21] Appl. No.: 766,109

[22] Filed: Aug. 15, 1985

[51] Int. Cl.$^5$ .................. C12N 15/00; C12N 9/64; C07H 15/12

[52] U.S. Cl. .................. 435/320; 435/172.3; 435/226; 435/252.33; 536/27; 935/14; 935/29; 935/73

[58] Field of Search ............... 435/68, 70, 172.3, 317; 536/27; 935/11, 29, 31, 38, 56, 60, 72, 73

[56] References Cited

U.S. PATENT DOCUMENTS 4,775,624 10/1988 Bang et al. .................. 435/226
4,784,950 11/1988 Hagen et al. .................. 435/68

FOREIGN PATENT DOCUMENTS 138222 4/1985 European Pat. Off.
WO85/00521 2/1985 United Kingdom.

OTHER PUBLICATIONS

Stenflo et al., (1982), *Journal of Biochemistry*, vol. 257, pp. 12180–12190.
Ferlund et al., (1982), *Journal of Biochemistry*, vol. 257, pp. 12170–12179.
Beckmann et al., (1985, Jul. 25), *Nucleic Acids Research*, vol. 13, pp. 6233–6247.
Foster and Davie, (1984), *Proceedings National Academy Sciences*, U.S.A., vol. 81, pp. 4766–4770.
Foster et al., (1985), *Proceedings National Academy Science*, U.S.A., vol. 82, pp. 4673–4677.
Degan et al., (1983), *Biochemistry*, vol. 22, pp. 2087–2092.
Foster, D. and E. Davie, Aug. 1984, PNAS, 81:4766–4770.
Foster, D. et al., Jul. 1985, PNAS, 82:4673–4677.
Long, G., et al., Sep. 1984, PNAS, 81:5653–5656.
Degan, S. et al., 1983, Biochem. 22:2087.

Kaufman and Sharp, *Mol. and Cell. Biol.*, 2:1304–1319, 1982.
Kaufman, *Proc. Natl. Acad. Sci.*, (U.S.A.), 82:689–693, 1985.
Hermonat et al., *Proc. Natl. Acad. Sci.*, (U.S.A.), 81:6466–6740, 1984.
Esmon et al., *Proc. Natl. Acad. Sci.*, (U.S.A.), 78:2249–2252, 1981.
Ginsburg et al., *Science*, 228:1401–1406, 1985.
Katayama et al., *Proc. Natl. Acad. Sci.*, (U.S.A.), 76:4990–4994, 1979.
Kisiel et al., *Biochem.*, 16:5824–5831, 1977.
Long et al., *Proc. Natl. Acad. Sci.*, (U.S.A.), 81:5653–5656, 1984.
Walker et al., *Biochim. et Biophys. Acta*, 571:333–342, 1979.
McMullen et al., *Biochem. and Biophys. Res. Comm.*, 115:8–14, 1983.
Beckmann et al., *Fed. Proc.*, 44:1069, 1985.
W. Kisiel et al., "Protein C", *Methods of Enzymology*, 80:320–332, 1981.
J. H. Griffin et al., "Deficiency of Protein C in Congential Thrombotic Disease", *J. Clin. Invest.*, 68:1370–1373, 1981.
Walter Kisiel, "Human Plamsa Protein C", *J. Clin. Invest.*, 64:761–769, 1979.
V. W. M. van Hinsbergh et al., "Activated Protein C Decreases Plasminogen Activator-Inhibitor Activity in Endothelial Cell-Conditioned Medium", *Blood*, 65:444–451, Feb. 1985.
W. Kisiel et al., "Enzymological Aspects of Blood Coagulation", *Behring Inst. Mitt.*, 73:29–42, 1983.

(List continued on next page.)

*Primary Examiner*—Thomas D. Mays
*Attorney, Agent, or Firm*—Seed and Berry

[57] ABSTRACT

Genomic and cDNA sequences coding for a protein having substantially the same biological activity as human protein C are disclosed. Recombinant plasmids and bacteriophage transfer vectors incorporating these sequences are also disclosed.

3 Claims, 5 Drawing Sheets

OTHER PUBLICATIONS

J. E. Gardiner and J. H. Griffin, "Human Protein C and Thromboembolic Disease", *Progress in Hematology*, pp. 265-278, 1983.

Philip C. Comp et al., "Generation of Fibrinolytic Activity by Infusion of Activated Protein C into Dogs", *J. Clin. Invest.*, 68:1221-1228, 1981.

Y. Sakata et al., "Activated Protein C Stimulates the Fibrinolytic Activity of Cultured Endothelial Cells and Decreases Antiactivator Activity", *Proc. Natl. Acad. Sci. U.S.A.*, 82:1121-1125, 1985.

A. Broekmans et al., "Congential Protein C Deficiency and Venous Thromboembolism", *The New England Journal of Medicine*, 309:340-344, 1983.

U. Seligsohn et al., "Homozygous Protein C Deficiency Manifested by Massive Venous Thrombosis in the Newborn", *The New England Journal of Medicine*, 310:559-562, 1984.

R. A. Marlar, "Mechanism of Action of Human Activated Protein C, a Thrombin-Dependent Anticoagulant Enzyme", *Blood*, 59:1067-1072, 1982.

```
                      -42          -40                                                        -30
                      Met Trp Gln Leu Thr Ser Leu Leu Phe Val Ala Thr
                      CGC CCA ACT TCC AGT ATC TCC ACC CCC AGT CCC TGT CCC ACA AGC CTC CTC TTC GTG CCC ACC              39

-20                                                        -10                                                  -1  +1
    Trp Gly Ile Ser Gly Thr Pro Ala Pro Leu Asp Ser Val Phe Ser Ser Glu Arg Ala His Gln Val Leu Arg Ile Arg Lys Arg Ala
    TGG GGA ATT TCC CCC ACA CCA GCT CCT CTT GAC TCA GTC TTC TCC AGC GAG CGG GCC CAC CAG GTG CTG CGG ATC CGG AAA CGT GCC          129

10                                                    20                                                30
    Asn Ser Phe Leu Glu Glu Leu Arg His Ser Ser Leu Glu Arg Glu Cys Ile Glu Ile Cys Asp Phe Glu Glu Ala Lys Glu Ile Phe
    AAC TCC TTC CTG GAG GAG CTC CGG CAC AGC AGC CTG GAG CGG GAG TGC ATA GAG ATC TGC GAC TTC GAG GAG GCC AAG GAA ATT TTC          219

40                                                    50                                                60
    Gln Asn Val Asp Asp Thr Leu Ala Phe Trp Ser Lys His Val Asp Gly Asp Gln Cys Leu Val Leu Pro Leu Glu His Pro Cys Ala Ser
    CAA AAT GTC GAT GAC ACA CTG GCC TTC TGG TCC AAG CAC GTC GAC GGT GAC CAG TGC TTG GTC CTT CCC TTG GAG CAC CCC TGC GCC AGC      309

70                                                    80                                                90
    Leu Cys Cys Gly His Gly Thr Cys Ile Asp Gly Ile Gly Ser Phe Ser Cys Asp Cys Arg Ser Gly Trp Glu Gly Arg Phe Cys Gln Arg
    CTC TGC TGC GGG CAC GGC ACC TGC ATC GAC GGC ATC GGC AGC TTC AGC TGC GAC TGC CGC AGC GGC TGG GAG GGC CGC TTC TGC CAG CGC      399

100                                                    110                                              120
    Glu Val Ser Phe Leu Asn Cys Ser Leu Asp Asn Gly Gly Cys Thr His Tyr Cys Leu Glu Glu Val Gly Trp Arg Arg Cys Ser Cys Ala
    GAG GTC AGC TTC CTC AAT TGC TCT CTG GAC AAC GGC GGC TGC ACC CAT TAC TGC CTA GAG GAG GTG GGC TGG CGG CGC TGT AGC TGC GCG      489

130                                                    140                                              150
    Pro Gly Tyr Lys Leu Gly Asp Asp Leu Leu Gln Cys His Pro Ala Val Lys Phe Pro Cys Gly Arg Pro Trp Lys Arg Met Glu Lys Lys
    CCT GGC TAC AAG CTG GGG GAC GAC CTC CTG CAG TGT CAC CCA GCA GTG AAG TTC CCT TGT GGG AGG CCG TGG AAG CGG ATG GAG AAG AAG      579

160                                           170
    Arg Ser His Leu Lys Arg Asp Thr Glu Asp Gln Glu Asp Gln Val Asp Pro Arg Leu Ile Asp Gly Lys Met Thr Arg Arg Gly Asp Ser
    CGC AGT CAC CTG AAA CGA GAC ACA GAA GAC CAA GAA GAC CAA GTA GAT CCT CGG CTC ATT GAT GGG AAG ATG ACC AGG CGG GGA GAC AGC      669
```

```
                                                                                                        210
                                             190                              200
Pro Trp Gln Val Leu Leu Asp Ser Lys Lys Leu Ala Cys Gly Ala Val Leu Ile His Pro Ser Trp Val Leu Thr Ala His     759
CCC TGG CAG GTG CTC CTC GAC TCA AAG AAG CTG GCC TGC GGG GCA GTG CTC ATC CAC CCC TCC TGG GTG CTG ACA GCG CAC 220                              230                              240
Cys Met Asp Glu Ser Lys Lys Leu Leu Val Arg Leu Gly Glu Tyr Asp Leu Arg Trp Glu Lys Trp Glu Leu Asp Leu Ile Lys     849
TGC ATG GAC GAG TCC AAG AAG CTC CTT GTC AGG CTT GGA GAG TAT GAC CTG CGG TGG GAG AAG TGG GAG CTG GAC CTG ATC AAG 250                              260                              270
Glu Val Phe Val His Pro Asn Tyr Ser Lys Ser Thr Thr Asp Asn Asp Ile Ala Leu Leu His Leu Ala Gln Pro Ala Thr Leu Ser Gln     939
GAG GTC TTC GTC CAC CCC AAC TAC TCC AAG AGC ACC ACC GAC AAT GAC ATC GCA CTG CTG CAC CTG GCC CAG CCC GCC ACC CTC TCG CAG 280                              290                              300
Thr Ile Val Pro Ile Cys Leu Pro Asp Ser Gly Leu Ala Glu Arg Glu Leu Asn Gln Ala Gly Gln Glu Thr Leu Val Thr Gly Trp Gly    1029
ACC ATA GTG CCC ATC TGC CTC CCC GAC AGC GGC CTT GCA GAG CGC GAG CTC AAT CAG GCC GGC CAG GAG ACC CTC GTG ACG GGC TGG GGC 310                              320                              330
Tyr His Ser Ser Arg Glu Lys Glu Ala Lys Arg Asn Arg Thr Phe Val Leu Asn Phe Ile Lys Ile Pro Val Val Pro His Asn Glu Cys    1119
TAC CAC AGC AGC CGA GAG AAG GAG GCC AAG AGA AAC CGC ACC TTC GTC CTC AAC TTC ATC AAG ATT CCC GTG GTC CCC CAC AAT GAG TGC 340                              350                              360
Ser Glu Val Met Ser Asn Met Val Ser Glu Asn Met Leu Cys Ala Gly Ile Leu Gly Asp Arg Gln Asp Ala Cys Glu Gly Asp Ser Gly    1209
AGC GAG GTC ATG AGC AAC ATG GTG TCT CAG AAC ATG CTG TGT GCC GGG ATC CTC GGG GAC CGG CAG GAC GCC TGC GAG GGC GAC AGT GGG 370                              380                              390
Gly Pro Met Val Ala Ser Phe His Gly Thr Trp Phe Leu Val Gly Leu Val Ser Trp Gly Glu Gly Cys Gly Leu Leu His Asn Tyr Gly    1299
GGG CCC ATG GTG GCC TCC TTC CAC GGC ACC TGG TTC CTG GTG GGC CTC GTG AGC TGG GGT GAG GGC TGT GGG CTT CTT CAC AAC TAC GGC 400                              410                              419
Val Tyr Thr Lys Val Ser Arg Tyr Leu Asp Trp Ile His Gly His Ile Arg Asp Lys Glu Ala Pro Gln Lys Ser Trp Ala Pro STOP    1389
GTT TAC ACC AAA GTC AGC CGC TAC CTC GAC TGG ATC CAT GGG CAC ATC AGA GAC AAG GAA GCC CCC CAG AAG AGC TGG GCA CCT TAC CGA
```

FIG. 3 CONT.

```
CCC TCC CTG CAG GGC TGG GCT TTT GCA TCG CAA TGG ATG GCA CAT TAA AGG GAC ATG TAA CAA GCA CAC CGG CCT GCT GTT CTG TCC TTC  1479

CAT CCC TCT TTT GGG CTC TTC TCG AGG GAA GTA ACA TTT ACT GAG CAC CTG TTG TAT GTC ACA TGC CTT ATG AAT AGA ATC TTA ACT CCT  1569

AGA GCA ACT CTG TCG GGT CGG GAG GAG CAG ATC CAA GTT TTC CGG GGT CTA AAG CTC TCT GTC TTG AGG GGG ATA CTC TCT TTA TGA AAA  1659

AGA ATA AAA AAC ACA ACC ACG AAA AAA AAA 3'  1689
```

FIG. 3 CONT.

DNA SEQUENCE CODING FOR PROTEIN C

TECHNICAL FIELD

The present invention relates to sequences coding for plasma proteins in general and, more specifically, to a DNA sequence which codes for a protein having substantially the same structure and/or activity of human protein C.

BACKGROUND ART

Protein C is a zymogen, or precursor, of a serine protease which plays an important role in the regulation of blood coagulation and generation of fibrinolytic activity in vivo. It is synthesized in the liver as a single-chain polypeptide which undergoes considerable processing to give rise to a two-chain molecule comprising heavy (Mr=40,000) and light (Mr=21,000) chains held together by disulphide bonds. The circulating two-chain intermediate is converted to the biologically active form of the molecule, known as "activated protein C" (APC), by the thrombin-mediated cleavage of a 12-residue peptide from the amino-terminus of the heavy chain. The cleavage reaction is augmented in vivo by thrombomodulin, an endothelial cell cofactor (Esmon and Owen, *Proc. Natl. Acad. Sci. USA* 78: 2249-2252, 1981).

Protein C is a vitamin K-dependent glycoprotein which contains approximately eleven residues of gammacarboxyglutamic acid (gla) and one equivalent of betahydroxyaspartic acid which are formed by post-translational modifications of glutamic acid and aspartic acid residues, respectively. The post-translational formation of specific gamma-carboxyglutamic acid residues in protein C requires vitamin K. These unusual amino acid residues bind to calcium ions and are believed to be responsible for the interaction of the protein with phospholipid, which is required for the anticoagulant activity of protein C.

In contrast to the coagulation-promoting action of other vitamin K-dependent plasma proteins, such as factor VII, factor IX, and factor X, activated protein C acts as regulator of the coagulation process through the inactivation of factor Va and factor VIIIa by limited proteolysis. The inactivation of factors Va and VIIIa by protein C is dependent upon the presence of acidic phospholipids and calcium ions. Protein S has been reported to regulate this activity by accelerating the APC-catalyzed proteolysis of factor Va (Walker, *J. Biol. Chem.* 255: 5521-5524, 1980).

Protein C has also been implicated in the action of plasminogen activator (Kisiel and Fujikawa, *Behring Inst. Mitt.* 73: 29-42, 1983). Infusion of bovine APC into dogs results in increased plasminogen activator activity (Comp and Esmon, *J. Clin. Invest.* 68: 1221-1228, 1981). Recent studies (Sakata et al., *Proc. Natl. Acad. Sci. USA* 82: 1121-1125, 1985) have shown that addition of APC to cultured endothelial cells leads to a rapid, dose-dependent increase in fibrinolytic activity in the conditioned media, reflecting increases in the activity of both urokinase-related and tissue-type plasminogen activators by the cells. APC treatment also results in a dose-dependent decrease in antiactivator activity.

Inherited protein C deficiency is associated with recurrent thrombotic disease (Broekmans et al., *New Eng. J. Med.* 309: 340-344, 1983; and Seligsohn et al., *New Eng. J. Med.* 310: 559-562, 1984) and may result from genetic disorder or from trauma, such as liver disease or surgery. This condition is generally treated with oral anti-coagulants. Beneficial effects have also been obtained through the infusion of protein C-containing normal plasma (see Gardiner and Griffin in *Prog. in Hematology*, ed. Brown, Grune & Stratton, NY, 13: 265-278). In addition, some investigators have discovered that the anti-coagulant activity of protein C is useful in treating thrombotic disorders, such as venous thrombosis (WO 85/00521). In some parts of the world, it is estimated that approximately 1 in 16,000 individuals exhibit protein C deficiency. Further, a total deficiency in protein C is fatal in newborns.

While natural protein C may be purified from clotting factor concentrates (Marlar et al., *Blood* 59: 1067-1072) or from plasma (Kisiel, ibid), it is a complex and expensive process, in part due to the limited availability of the starting material and the low concentration of protein C in plasma. Furthermore, the therapeutic use of products derived from human blood carries the risk of disease transmission by, for example, hepatitis virus, cytomegalovirus, or the causative agent of acquired immune deficiency syndrome (AIDS). In view of protein C's clinical applicability in the treatment of thrombotic disorders, the production of useful quantities of protein C and activated protein C is clearly invaluable.

DISCLOSURE OF INVENTION

Briefly stated, the present invention discloses a DNA sequence which codes for a protein having substantially the same biological activity as human protein C.

In addition, the present invention discloses a recombinant plasmid or bacteriophage transfer vector comprising a cDNA sequence comprising the protein C gene cDNA sequence. The amino acid and DNA sequences of this cDNA coding for human protein C are also disclosed.

Other aspects of the invention will become evident upon reference to the detailed description and attached drawings.

BRIEF DESCRIPTION OF THE DRAWINGS

FIG. 2 illustrates the complete genomic sequence, including exons and introns for human protein C. Arrowheads indicate intron-exon splice junctions. The polyadenylation or processing sequences of A-T-T-A-A-A and A-A-T-A-A-A at the 3' end are boxed. ◆, potential carbohydrate binding sites; ✓, apparent cleavage sites for processing of the connecting dipeptide; ↓, site of cleavage in the heavy chain when protein C is converted to activated protein C; ●, sites of polyadenylation.

FIG. 3 depicts the amino acid and DNA sequences for a cDNA coding for human protein C.

BEST MODE FOR CARRYING OUT THE INVENTION

Figure 1:
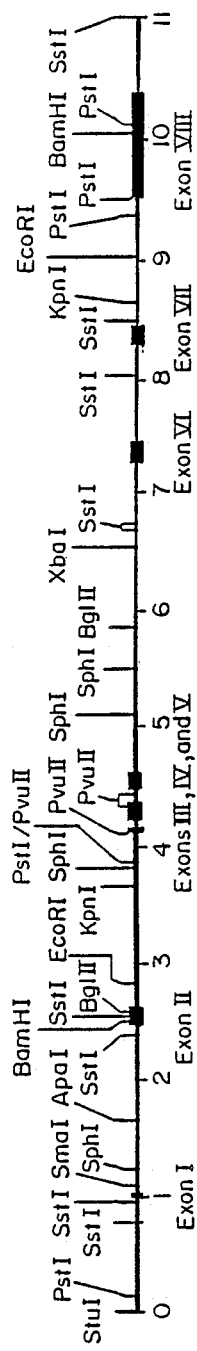
FIG. 1 illustrates a restriction enzyme map of the genomic DNA coding for human protein C.

Prior to setting forth the invention, it may be helpful to an understanding thereof to set forth definitions of certain terms to be used hereinafter.

Biological Activity: A function or set of functions performed by a molecule in a biological context (i.e., in an organism or an in vitro facsimile). Biological activities of proteins may be divided into catalytic and effector activities. Catalytic activities of the vitamin K-dependent plasma proteins generally involve the specific proteolytic cleavage of other plasma proteins, resulting in activation or deactivation of the substrate. Effector activities include specific binding of the biologically active molecule to calcium or other small molecules, to macromolecules, such as proteins, or to cells. Effector activity frequently augments, or is essential to, catalytic activity under physiological conditions.

For protein C, biological activity is characterized by its anticoagulant and fibrinolytic properties. Protein C, when activated, inactivates factor Va and factor VIIIa in the presence of phospholipid and calcium. Protein S appears to be involved in the regulation of this function (Walker, ibid). Activated protein C also enhances fibrinolysis, an effect believed to be mediated by the lowering of levels of plasminogen activator inhibitors (van Hinsbergh et al., Blood 65: 444-451, 1985). As more fully described below, Exons VII and VIII are primarily responsible for the catalytic activity of protein C.

Transfer Vector: A DNA molecule which contains, inter alia, genetic information which ensures its own replication when transferred to a host microorganism strain. Examples of transfer vectors commonly used for recombinant DNA are plasmids and certain bacteriophages. Transfer vectors normally include an origin of replication and sequences necessary for efficient transcription and translation of DNA.

As noted above, protein C is synthesized as a single-chain polypeptide which undergoes considerable processing to give rise to a two-chain molecule; a heavy chain ($M_r$ 41,000) and a light chain ($M_r$ 21,000), held together by a disulfide bond.

Within the present invention, a λgt11 cDNA library was prepared from human liver mRNA. This library was then screened with $125_I$ labeled antibody to human protein C. Antibody-reactive clones were further analyzed for the synthesis of a fusion protein of B-galactosidase and protein C in the λgt11 vector.

One of the clones gave a strong signal with the antibody probe and was found to contain an insert of approximately 1400 bp. DNA sequence analysis of the DNA insert revealed a predicted amino acid sequence which shows a high degree of homology to major portions of the bovine protein C, as determined by Fernlund and Stenflo (*J. Biol. Chem.* 257: 12170-12179; *J. Biol. Chem.* 257: 12180-12190). Chem. 257: 12170

The DNA insert contained the majority of the coding region for protein C beginning with amino acid 65 of the light chain, including the entire heavy chain coding region, and proceeding to the termination codon. Further, following the stop codon of the heavy chain, there are 294 base pairs of 3' noncoding sequence and a poly (A) tail of 9 base pairs. The processing or polyadenylation signal A-A-T-A-A-A was present 13 base pairs upstream from the poly (A) tail in this cDNA insert. This sequence is one of two potential polyadenylation sites.

The cDNA sequence also contains the dipeptide Lys-Arg at position 156-157, which separates the light chain from the heavy chain and is removed during processing by proteolytic cleavage. Upon activation by thrombin, the heavy chain of human protein C is cleaved between arginine-12 and leucine-13, releasing the activation peptide.

In order to obtain the remainder of the light chain coding sequence (amino acids 1-64), a human genomic library in λ Charon 4A phage was screened for genomic clones of human protein C using the cDNA described above as a hybridization probe. Three different λ Charon 4A phage were isolated that contained overlapping inserts for the gene coding for protein C.

The position of exons on the three phage clones were determined by Southern blot hybridization of digests of these clones with probes made from the 1400 bp cDNA described above. The genomic DNA inserts in these clones were mapped by single and double restriction enzyme digestion followed by agarose gel electrophoresis, Southern blotting, and hybridization to radiolabeled 5' and 3' probes derived from the cDNA for human protein C, as shown in FIG. 1.

Figure 2:
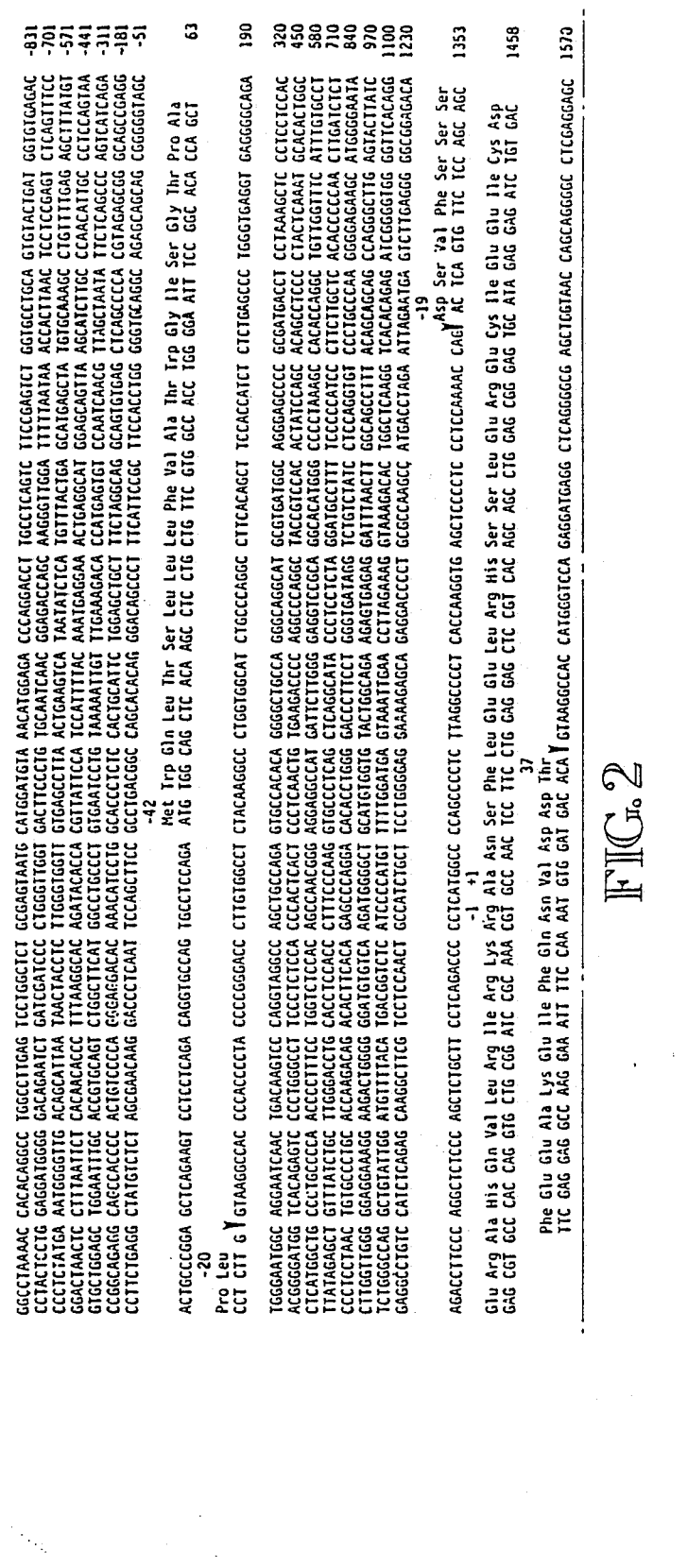
Figure 2:
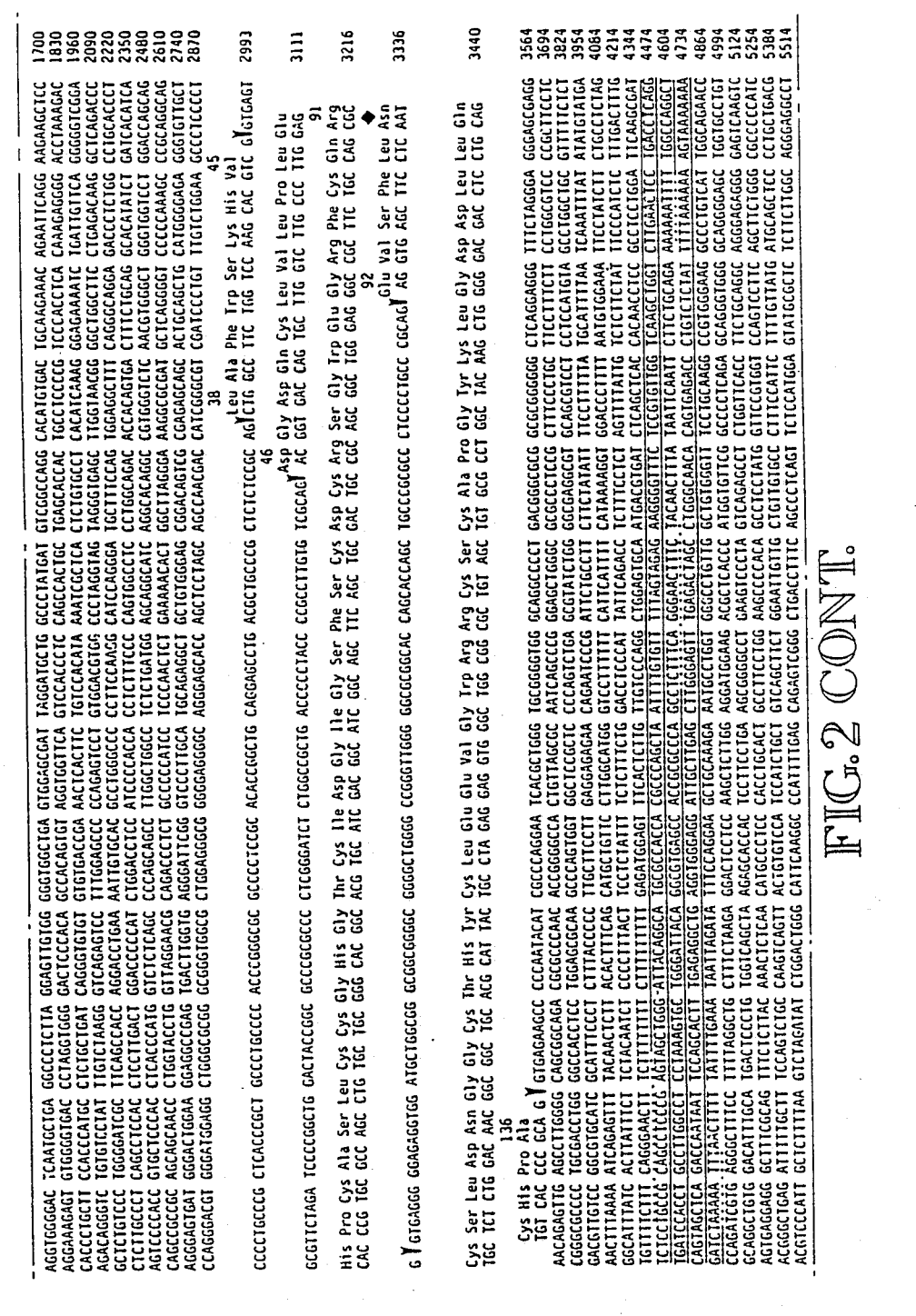
Figure 2:
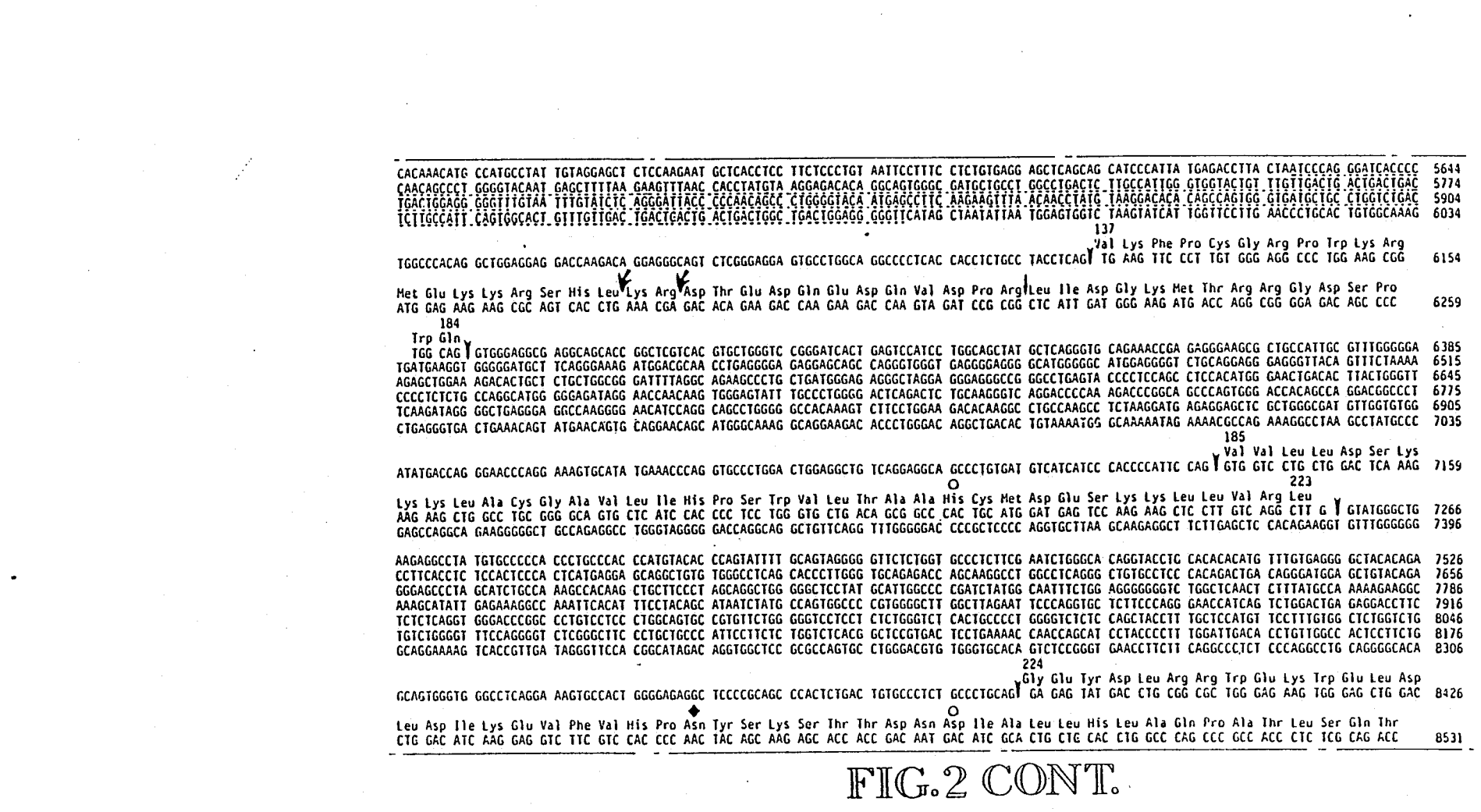
Figure 2:
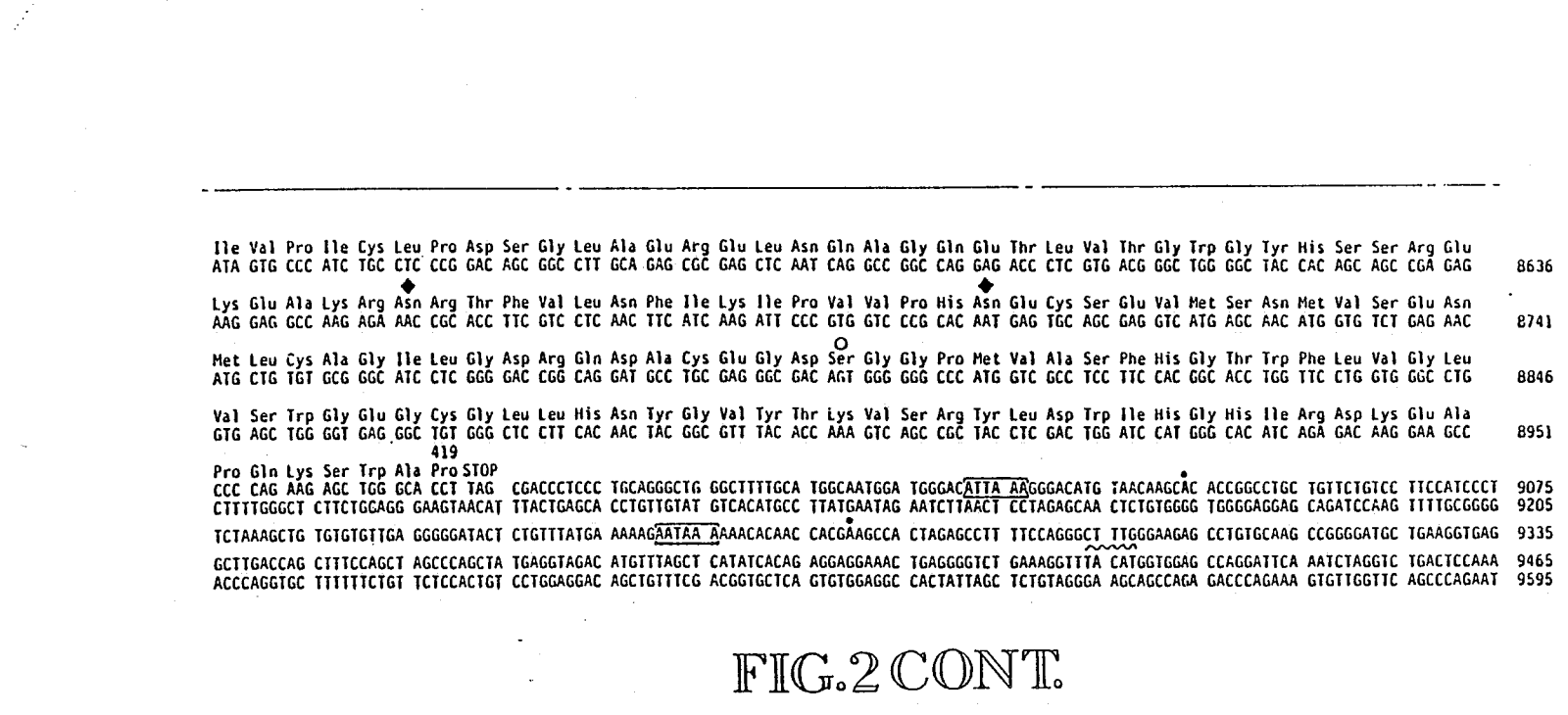

DNA sequencing studies were performed using the dideoxy chain-termination method. As shown in FIG. 2, the nucleotide sequence for the gene for human protein C spans approximately 11 kb of DNA. These studies further revealed a potential pre-pro leader sequence of 42 amino acids. Based on homology with the leader sequence of bovine protein C in the region −1 to −20, it is likely that the pre-pro leader sequence is cleaved by a signal peptidase following the Ala residue at position −10. Processing to the mature protein involves additional proteolytic cleavage following residue −1 to remove the amino-terminal propeptide, and at residues 155 and 157 to remove the Lys-Arg dipeptide which connects the light and heavy chains. This final processing yields a light chain of 155 amino acids and a heavy chain of 262 amino acids.

As noted above, the protein C gene is composed of eight exons ranging in size from 25 to 885 nucleotides, and seven introns ranging in size from 92 to 2668 nucleotides. Exon I and a portion of Exon II code for the 42 amino acid pre-pro peptide. The remaining portion of Exon II, Exon III, Exon IV, Exon V, and a portion of Exon VI code for the light chain of protein C. The remaining portion of Exon VI, Exon VII, and Exon VIII code for the heavy chain of protein C. The amino acid and DNA sequences for a cDNA coding for human protein C are shown in FIG. 3.

The location of the introns in the gene for protein C are primarily between various functional domains. Exon II spans the highly conserved region of the leader sequence and the gamma-carboxyglutamic acid (gla) domain. Exon III includes a stretch of eight amino acids which connect the Gla and growth factor domains. Exons IV and V each represent a potential growth factor domain, while Exon VI covers a connecting region which includes the activation peptide. Exons VII and VIII cover the catalytic domain typical of all serine proteases.

Figure 4:
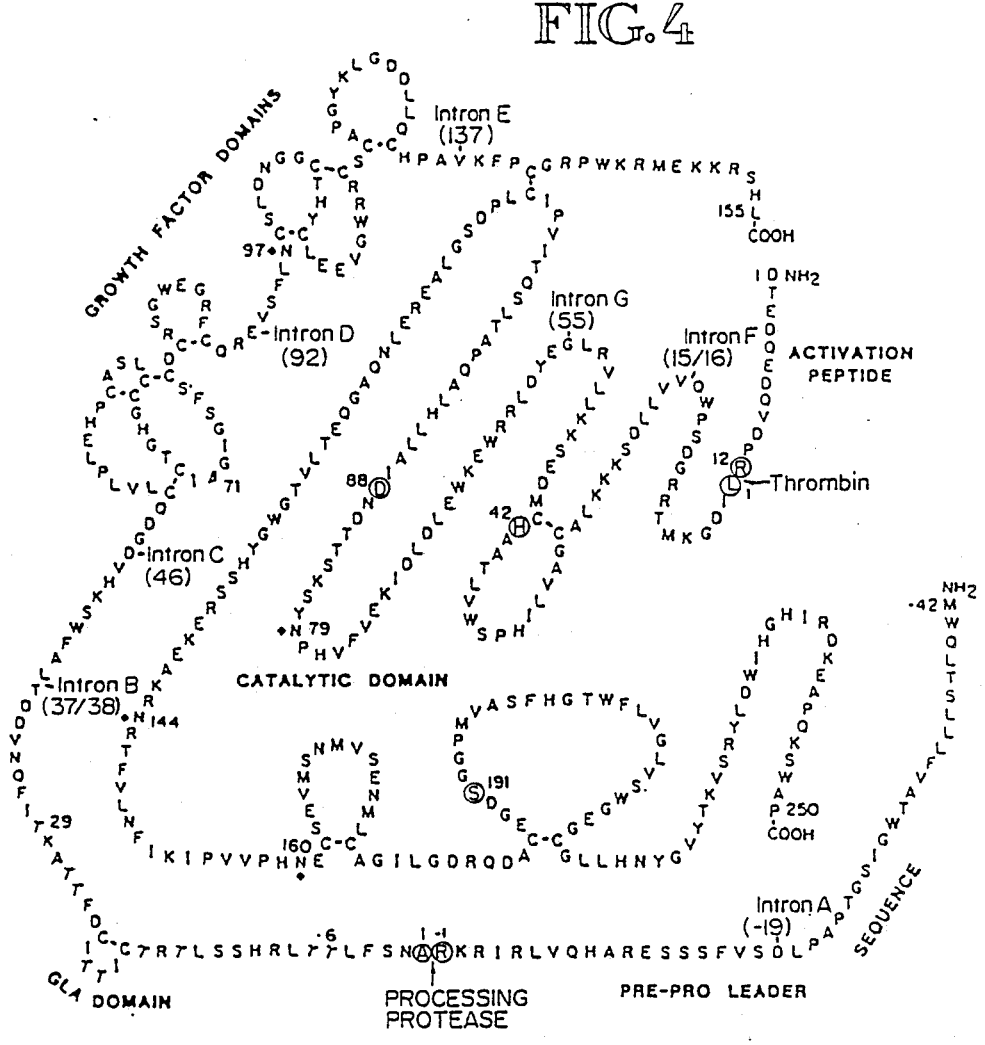
FIG. 4 illustrates a proposed model for the structure of human protein C.

The amino acid sequence and tentative structure for human pre-pro protein C are shown in FIG. 4. Protein C is shown without the Lys-Arg dipeptide, which connects the light and heavy chains. The location of the seven introns (A through G) is indicated by solid bars. Amino acids flanking known proteolytic cleavage sites are circled. ◆designates potential carbohydrate binding sites. The first amino acid in the light chain, activation peptide, and heavy chain start with number 1, and differ from that shown in FIGS. 2 and 3.

Carbohydrate attachment sites are located at residue 97 in the light chain and residues 79, 144, and 160 in the heavy chain, according to the numbering scheme of FIG. 4. The carbohydrate moiety is covalently linked to Asn, but Thr, Ser, or Gln may be substituted. In the majority of instances, the carbohydrate attachment environment can be represented by N-X-Ser or N-X-

Thr, where N=Asn, Thr, Ser, or Gln, and X=any amino acid.

The catalytic domain of protein C, which is encoded by Exons VII and VIII, plays a regulatory role in the coagulation process. This domain possesses serine protease activity which specifically cleaves certain plasma proteins (i.e., factors Va and VIIIa), resulting in their acrivation or deactivation. As a result of this selective proteolysis, protein C displays anticoagulant and fibrinolytic activities.

The example which follows describes the cloning of DNA sequences encoding human protein C.

EXAMPLE

Restriction endonucleases and other DNA modification enzymes (e.g., T4 polynucleotide kinase, bacterial alkaline phosphatase, Klenow DNA polymerase, T4 polynucleotide ligase) may be obtained from Bethesda Research Laboratories (BRL) and New England Biolabs and are used as directed by the manufacturer, unless otherwise noted.

CLONING OF DNA SEQUENCES ENCODING HUMAN PROTEIN C

A cDNA coding for a portion of human was prepared as described by Foster and Davie (PNAS (USA) 81: 4766–4770, 1984, herein incorporated by reference). Briefly, a λgtll cDNA library was prepared from human liver mRNA by conventional methods. Clones were screened using 125$_I$-labeled affinity-purified antibody to human protein C, and phage were prepared from positive clones by the plate lysate method (Maniatis et al., ibid), followed by banding on a cesium chloride gradient. The cDNA inserts were removed using Eco RI and subcloned into plasmid pUC9 (Vieira and Messing, *Gene* 19: 259–268, 1982). Restriction fragments were subcloned in the phage vectors M13mp10 and m13mpll (Messing, *Meth. in Enzymology* 101: 20–77, 1983) and sequenced by the dideoxy method (Sanger et al., *Proc. Natl. Acad. Sci. USA* 74: 5463–5467, 1977). A clone was selected which contained DNA corresponding to the known sequence of human protein C (Kisiel, ibid) and encoded protein C beginning at amino acid 65 of the light chain and extending through the heavy chain and into the 3' non-coding region. This clone was designated λHC1375.

The cDNA insert from λHC1375 was nick translated using α—$^{32}$P dNTP's and used to probe a human genomic library in phage λ Charon 4A (Maniatis et al., *Cell* 15: 687–702, 1978) using the plaque hybridization procedure of Benton and Davis (*Science* 196: 181–182, 1977) as modified by Woo (*Meth. in Enzymology* 68: 381–395, 1979). Positive clones were isolated and plaque-purified (by Foster et al., *PNAS* (USA) 82: 4673–4677, 1985, herein incorporated by reference).

Phage DNA was prepared from positive clones by the method of Silhavy et al. (Experiments with Gene Fusion, Cold Spring Harbor Laboratory, 1984). The purified phage DNA was digested with EcoRI and subcloned into pUC9 for further mapping and sequencing studies. Further analysis suggested that the gene for protein C was present in three EcoRI fragments. In order to generate overlapping protein C DNA sequences, purified phage DNA was digested with Bgl II and subcloned into pUC9.

The sequences of the EcoRI and Bgl II protein C fragments were determined by subcloning the fragments into M13 phage cloning vectors. Sequence analysis of the overlapping fragments established the DNA sequence of the entire protein C gene.

Alternatively, the complete DNA sequence has been determined using a second cDNA clone isolated from a λgtll cDNA library. This clone encodes a major portion of protein C, beginning at amino acid 24 and including the heavy chain coding region, termination codon, and 3' noncoding region. The insert from this λ phage clone was subcloned into pUC9 and the resultant plasmid designated pHC 6L.

This pHC 6L insert was nick translated and used to probe a human genomic library in phage λ Charon 4A. One genomic clone was identified which contained a 4.4 kb EcoRI fragment corresponding to the 5' end of the protein C gene. This phage clone was subcloned into pUC9 and the resultant plasmid designated pHCR 4.4. DNA sequence analysis revealed that the pHCR 4.4 insert comprised two exons, encoding amino acids −42 to −19, and amino acids −19 to 37. Thus, the DNA sequence of the entire protein C gene was established due to the overlapping sequences of pHC 6L (24 to 3' noncoding region) and pHCR 4.4 (−42 to 37).

From the foregoing it will be appreciated that, although specific embodiments of the invention have been described herein for purposes of illustration, various modifications may be made without deviating from the spirit and scope of the invention. Accordingly, the invention is not limited except as by the appended claims.

We claim:

1. An isolated human DNA sequence which codes for a protein having substantially the same biological activity as human protein C.

2. An isolated DNA sequence comprising the sequence of FIG. 2, from bp 1 to bp 8972, which sequence codes for human protein C.

3. A bacterial plasmid or bacteriophage transfer vector comprising a cDNA sequence comprising the human protein C gene cDNA sequence.

* * * * *

UNITED STATES PATENT AND TRADEMARK OFFICE
CERTIFICATE OF CORRECTION

PATENT NO : 4,968,626
DATED : Nov. 6, 1990
INVENTOR(S) : Donald C. Foster, Earl W. Davie It is certified that error appears in the above-identified patent and that said Letters Patent are hereby corrected as shown below:

At column 1 following the title, please add the following:

--GOVERNMENT SUPPORT

This invention was made with government support under National Institutes of Health grant number HL16919. The government has certain rights in the invention.--

Signed and Sealed this

Eighth Day of May, 2001

*Attest:*

NICHOLAS P. GODICI

*Attesting Officer*     *Acting Director of the United States Patent and Trademark Office*